United States Patent
Cheng et al.

(10) Patent No.: US 9,657,019 B2
(45) Date of Patent: May 23, 2017

(54) 1,9-DIAZAPHENALENE DERIVATIVE AND PROCESS FOR MANUFACTURING THE SAME

(71) Applicant: National Tsing Hua University, Hsinchu (TW)

(72) Inventors: Chien-Hong Cheng, Hsinchu (TW); Jayachandran Jayakumar, Hsinchu (TW); Min-Hsien Chen, Fangliao Township (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 14/683,346

(22) Filed: Apr. 10, 2015

(65) Prior Publication Data
US 2016/0185781 A1 Jun. 30, 2016

(30) Foreign Application Priority Data
Dec. 24, 2014 (TW) .............................. 103145258 A

(51) Int. Cl.
*C07D 471/06* (2006.01)
(52) U.S. Cl.
CPC ............................. *C07D 471/06* (2013.01)
(58) Field of Classification Search
CPC .................................................... C07D 471/06
USPC ........................................................... 546/81
See application file for complete search history.

(56) References Cited

FOREIGN PATENT DOCUMENTS

TW 263510 B 11/1995

OTHER PUBLICATIONS

Ao Yu et al. The effect of insertion of nitrogen atoms on the aromatic nitrogen-containing compounds: a ptential approach for designing stable radical molecular materials. 2011.*
One-Pot Synthesis of Highly Substituted Polyheteroaromatic Compounds by Rhodium(III)—Catalyzed Multiple C H Activation and Annulation . . . Jayachandran Jayakumar et al , Jul. 14, 2014.*
Jie Li et al Amidines for Versatile Ruthenium (II)-catalyzed Oxidative C—H Activations with internal Alkynes and Acrylates. Published Mar. 2014.*

* cited by examiner

*Primary Examiner* — Rita Desai
(74) *Attorney, Agent, or Firm* — Birch, Stewart, Kolasch & Birch, LLP

(57) ABSTRACT

A 1,9-diazaphenalene derivative is represented by

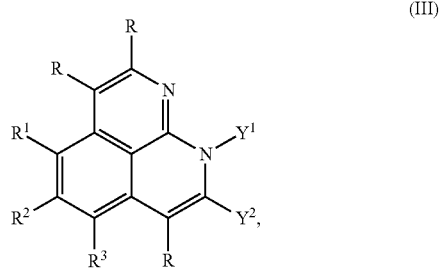

(III)

where R, $R^1$, $R^2$, $R^3$, $Y^1$, and $Y^2$ are as defined in the specification and claims. The 1,9-diazaphenalene derivative may emit fluorescence after being excited, and is thus suitable for use as a fluorescent material for an organic light emitting diode. A method for preparing the 1,9-diazaphenalene derivative is also disclosed.

7 Claims, 1 Drawing Sheet

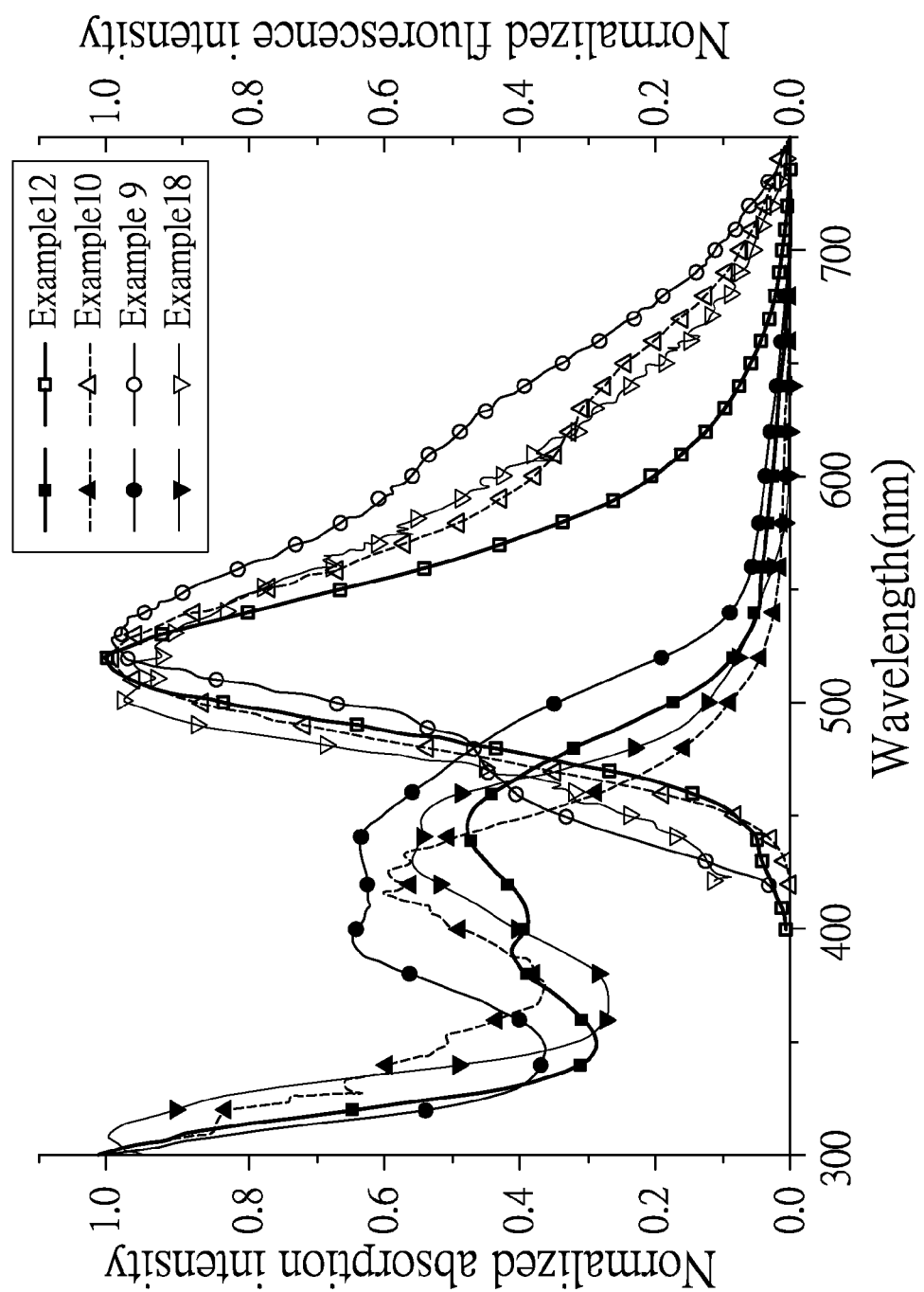

1,9-DIAZAPHENALENE DERIVATIVE AND PROCESS FOR MANUFACTURING THE SAME

CROSS-REFERENCE TO RELATED APPLICATION

This application claims priority of Taiwanese Application No. 103145258, filed on Dec. 24, 2014.

FIELD

The disclosure relates to a 1,9-diazaphenalene derivative, and more particularly to a 1,9-diazaphenalene derivative which is highly substituted. The disclosure also relates to a process for manufacturing the 1,9-diazaphenalene derivative.

BACKGROUND

Taiwanese Patent Publication No. 263510 discloses 1,8-benzo[b]naphthyridine derivative in which three aromatic rings are fused in a linear manner. The derivative is useful as an antimicrobial agent.

It is disclosed in *J. Org. Chem.*, 1990, 55, 6140-6147 a 1H-2,3-dihydro-1,9-diazaphenalene derivative of the following formula:

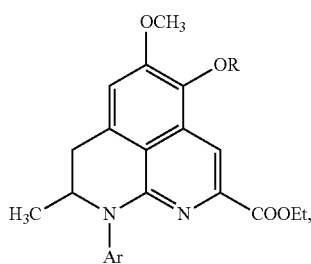

where Ar represents phenyl, 4-methylphenyl, 4-methoxyphenyl, 4-chlorophenyl or 4-fluorophenyl, and R represents hydrogen or benzyl. As shown in the above formula, not all of three fused cyclic moieties are aryl rings.

There is a need in the art for a 1,9-diazaphenalene derivative which contains a plurality of fused aryl rings and which is highly substituted.

SUMMARY

Therefore, an object of the disclosure is to provide a 1,9-diazaphenalene derivative which contains a plurality of fused aryl rings, which is highly substituted, and which may emit fluorescence after being excited.

Another object of the disclosure is to provide a process for manufacturing the 1,9-diazaphenalene derivative.

A 1,9-diazaphenalene derivative according to a first aspect of the disclosure is represented by formula (III)

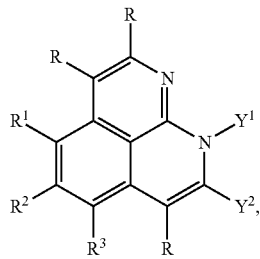

where
each R independently represents a $C_1$-$C_{10}$ linear or branched alkyl group, or a 5-6 membered aryl or heteroaryl group which is unsubstituted or substituted with a $C_1$-$C_{10}$ alkyl group, a $C_1$-$C_6$ alkoxy group, a $C_1$-$C_6$ haloalkyl group or a halo group;

each of $R^1$, $R^2$, and $R^3$ independently represents hydrogen, a $C_1$-$C_{10}$ linear or branched alkyl group, a $C_1$-$C_{10}$ alkoxy group, a $C_1$-$C_6$ haloalkyl group, an unsubstituted or $C_1$-$C_{10}$ alkyl group-substituted amino group, a halo group, a $C_6$-$C_{18}$ aryl group,

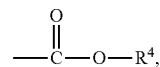

in which $R^4$ represents a $C_1$-$C_{10}$ alkyl group, or

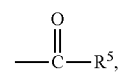

in which $R^5$ represents hydrogen or a $C_1$-$C_{10}$ alkyl group;

$Y^1$ represents hydrogen, or a $C_1$-$C_{10}$ linear or branched alkyl group;

$Y^2$ represents R; or $Y^1$ and $Y^2$ are combined to form a 6-membered ring moiety represented by

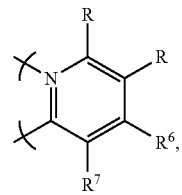

where
each of $R^6$ and $R^7$ independently represents a thio group, a heteroalkyl group, or a $C_1$-$C_{10}$ linear or branched alkyl group, or $R^6$ and $R^7$ are combined to form a 5-6 membered aryl or heteroaryl group represented by

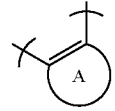

which is unsubstituted or substituted with a $C_1$-$C_{10}$ alkyl group, a $C_1$-$C_6$ alkoxy group, a $C_1$-$C_6$ haloalkyl group or a halo group.

A process for manufacturing the 1,9-diazaphenalene derivative of the aforesaid formula (III) according to a second aspect of the disclosure includes the step of subjecting a benzamidine derivative of formula (I)

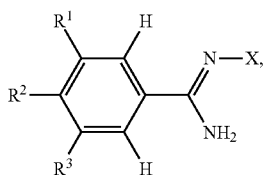
(I)

where
X represents hydrogen, hydroxyl, or a $C_1$-$C_{10}$ linear or branched alkyl group; and
$R^1$, $R^2$, and $R^3$ are defined as above,
and an alkyne compound of formula (II)

(II)

where R is defined as above,
to a catalystic reaction in the presence of an oxidant and a catalyst selected from the group consisting of a rhodium-containing complex and a ruthenium-containing complex.

A process for manufacturing the 1,9-diazaphenalene derivative of the aforesaid formula (III) according to a third aspect of the disclosure includes the step of subjecting a benzonitrile compound of formula (IV)

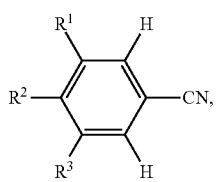
(IV)

where $R^1$, $R^2$, and $R^3$ are defined as above,
an amine compound of formula X—$NH_2$ (V), where X is defined as above,
and an alkyne compound of formula (II)

(II)

where R is defined as above,
to a catalystic reaction in the presence of an oxidant and a catalyst selected from the group consisting of a rhodium salt and a ruthenium salt.

A 1,9-diazaphenalene derivative which contains a plurality of fused aryl rings, which is highly substituted, and which may emit fluorescence after being excited may be manufactured in a high yield by the disclosure via a simple one-pot reaction.

BRIEF DESCRIPTION OF THE DRAWINGS

Other features and advantages of the disclosure will become apparent in the following detailed description of the embodiments with reference to the accompanying drawing, of which:

The FIGURE is an ultraviolet-visible spectrum illustrating absorption and fluorescence spectra of 1,9-diazaphenalene derivatives obtained in Examples 9, 10, 12 and 18.

DETAILED DESCRIPTION

A 1,9-diazaphenalene derivative according to the disclosure is represented by

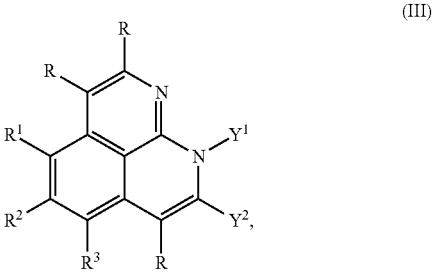
(III)

where
each R independently represents a $C_1$-$C_{10}$ linear or branched alkyl group, or a 5-6 membered aryl or heteroaryl group which is unsubstituted or substituted with a $C_1$-$C_{10}$ alkyl group, a $C_1$-$C_6$ alkoxy group, a $C_1$-$C_6$ haloalkyl group or a halo group;
each of $R^1$, $R^2$, and $R^3$ independently represents hydrogen, a $C_1$-$C_{10}$ linear or branched alkyl group, a $C_1$-$C_{10}$ alkoxy group, a $C_1$-$C_6$ haloalkyl group, an unsubstituted or $C_1$-$C_{10}$ alkyl group-substituted amino group, a halo group, a $C_6$-$C_{18}$ aryl group,

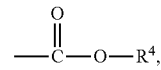

in which $R^4$ represents a $C_1$-$C_{10}$ alkyl group, or

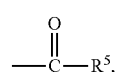

in which $R^5$ represents hydrogen or a $C_1$-$C_{10}$ alkyl group;
$Y^1$ represents hydrogen, or a $C_1$-$C_{10}$ linear or branched alkyl group;
$Y^2$ represents R; or
$Y^1$ and $Y^2$ are combined to form a 6-membered ring moiety represented by R

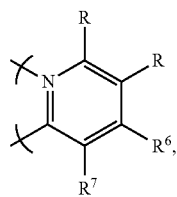

where each of $R^6$ and $R^7$ independently represents a thio group, a heteroalkyl group, or a $C_1$-$C_{10}$ linear or branched alkyl group, or $R^6$ and $R^7$ are combined to form a 5-6 membered aryl or heteroaryl group represented by

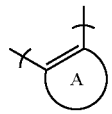

which is unsubstituted or substituted with a $C_1$-$C_{10}$ alkyl group, a $C_1$-$C_6$ alkoxy group, a $C_1$-$C_6$ haloalkyl group or a halo group.

A process for manufacturing the 1,9-diazaphenalene derivative of the aforesaid formula (III) according to the disclosure includes the step of subjecting a benzamidine derivative of formula (I)

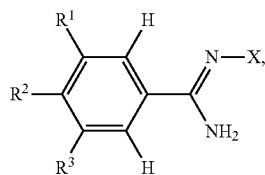

where

X represents hydrogen, hydroxyl, or a $C_1$-$C_{10}$ linear or branched alkyl group; and $R^1$, $R^2$, and $R^3$ are defined as above, and an alkyne compound of formula (II)

where R is defined as above
to a catalystic reaction in the presence of an oxidant and a catalyst selected from the group consisting of a rhodium-containing complex and a ruthenium-containing complex.

Alternatively, a process for manufacturing the 1,9-diazaphenalene derivative of the aforesaid formula (III) according to the disclosure includes the step of subjecting a benzonitrile compound of formula (IV)

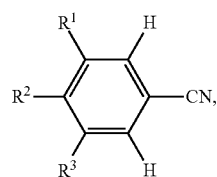

where $R^1$, $R^2$, and $R^3$ are defined as above,
an amine compound of formula X—$NH_2$ (V), where X is defined as above,
and an alkyne compound of formula (II),

where R is defined as above,
to a catalystic reaction in the presence of an oxidant and a catalyst selected from the group consisting of a rhodium salt and a ruthenium salt.

Preferably, each R independently represents a 5-6 membered aryl or heteroaryl group which is unsubstituted or substituted with a $C_1$-$C_{10}$ alkyl group, a $C_1$-$C_6$ alkoxy group, a $C_1$-$C_6$ haloalkyl group or a halo group.

More preferably, each R is independently selected from the group consisting of phenyl, 4-methylphenyl, 4-methoxyphenyl, 4-bromophenyl, 4-trifluoromethylphenyl and 2-thienyl.

In the process for manufacturing the 1,9-diazaphenalene derivative of formula (III), a molar ratio of the benzamidine derivative of formula (I) to the alkyne compound of formula (II) ranges preferably from 1:2 to 1:3.5 and more preferably from 1:3 to 1:3.5.

Preferably, the oxidant suitable for the disclosure is copper (II) compounds, such as copper (II) acetate, copper (II) acetate monohydrate and copper trifluoromethanesulfonate.

Preferably, the rhodium-containing complex suitable for the disclosure is a rhodium (III)-containing complex selected from the group consisting of [Cp*Rh($CH_3CN$)$_3$](SbF$_6$)$_2$ and [RhCp*Cl$_2$]$_2$, wherein Cp* represents pentamethylcyclopentadienyl.

Preferably, the ruthenium-containing complex is a ruthenium (II)-containing complex of [RuCl$_2$(p-cymene)]$_2$, wherein Cp* represents pentamethylcyclopentadienyl.

Preferably, the catalystic reaction is conducted in the presence of an organic solvent. The organic solvent suitable for the disclosure is selected from the group consisting of 2-methyl-2-butanol, dimethylformamide, o-xylene, dichloroethane, acetonitrile and acetic acid.

Preferably, X in formula (I) or formula (V) represents hydroxyl.

Preferably, the catalystic reaction is conducted at a temperature ranging from 120° C. to 130° C.

Preferably, the catalystic reaction is conducted for a period ranging from 18 hours to 42 hours.

A reaction scheme of the process for manufacturing the 1,9-diazaphenalene derivative of formula (III) is illustrated below, in which a rhodium (III)-containing complex is used as the catalyst, Cp* represents pentamethylcyclopentadienyl, X in formula (I) represents hydroxyl, and R in formula (II) represents phenyl,

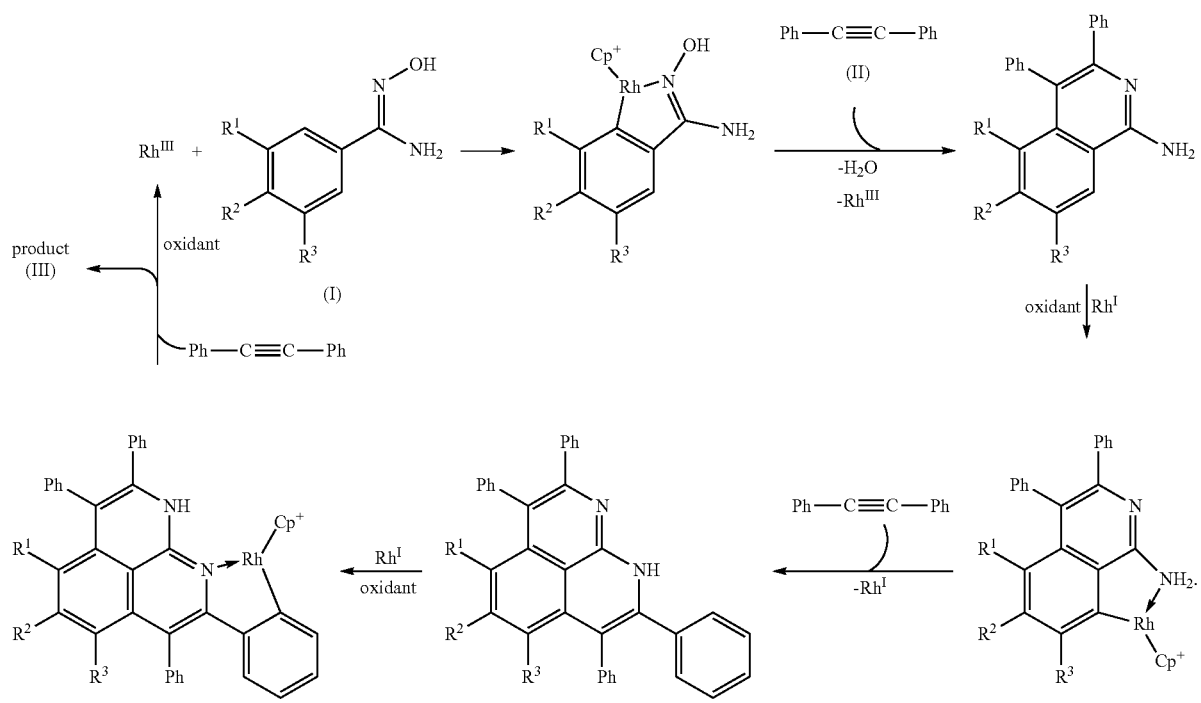

The following examples are provided to illustrate the embodiments of the disclosure, and should not be construed as limiting the scope of the disclosure.

Synthesis (I) of 1,9-Diazaphenalene Derivative

Examples 1-23

0.25 mmol of a benzamidine derivative of formula (I), 0.80 mmol of an alkyne compound of formula (II), 6.0 mol % of [Cp*Rh(CH$_3$CN)$_3$](SbF$_6$)$_2$ (Cp* represents pentamethylcyclopentadienyl), and 1.12 mmol (4.5 equivalents) of copper (II) acetate were added into a sealed tube. The sealed tube was then evacuated and purged with nitrogen gas three times. 3.5 ml of 2-methyl-2-butanol was subsequently added into the sealed tube via a syringe under a nitrogen atmosphere to obtain a reaction mixture, which was stirred at 130° C. for 18 hours. The mixture was then cooled and diluted with CH$_2$Cl$_2$ (10 ml), followed by filtration through a Celite pad. The Celite pad was washed with CH$_2$Cl$_2$ (50 ml) to obtain a filtrate. The filtrate was concentrated in vacuo and the residue was purified by a silica gel column using hexane-EtOAc (5-15%) as eluent to give a product of formula (III).

The definitions of R$^1$, R$^2$, R$^3$, X, R, Y$^1$, and Y$^2$ in formulae (I), (II), and (III) in Examples 1-23 are listed in Table 1.

TABLE 1

| | Formula (I) | | | | Formulae (II) and (III) | Formula (III) | | | |
|---|---|---|---|---|---|---|---|---|---|
| Ex. | R$^1$ | R$^2$ | R$^3$ | X | R | R$^1$ | R$^2$ | R$^3$ | Y$^1$ and Y$^2$ |
| 1 | H | H | H | OH | Ph | H | H | H | |
| 2 | H | Me | H | OH | Ph | H | Me | H | |
| 3 | H | tBu | H | OH | Ph | H | tBu | H | |
| 4 | H | OMe | H | OH | Ph | H | OMe | H | |
| 5 | H | F | H | OH | Ph | H | F | H | |
| 6 | H | Cl | H | OH | Ph | H | Cl | H | |
| 7 | H | Br | H | OH | Ph | H | Br | H | |
| 8 | H | I | H | OH | Ph | H | I | H | |
| 9 | H | CF$_3$ | H | OH | Ph | H | CF$_3$ | H | |
| 10 | H | N(Me)$_2$ | H | OH | Ph | H | N(Me)$_2$ | H | |
| 11 | H | Ph | H | OH | Ph | H | Ph | H | |
| 12 | OMe | OMe | OMe | OH | Ph | OMe | OMe | OMe | |
| 13 | OMe | H | H | OH | Ph | OMe | H | H | |
| | | | | | | H | H | OMe | |

TABLE 1-continued

| | Formula (I) | | | | Formulae (II) and (III) | Formula (III) | | | |
|---|---|---|---|---|---|---|---|---|---|---|
| Ex. | R¹ | R² | R³ | X | R | R¹ | R² | R³ | Y¹ and Y² | |
| 14 | H | H | H | OH | 4-MeC₆H₄ | H | H | H | | Z = Me |
| 15 | H | H | H | OH | 4-MeOC₆H₄ | H | H | H | | Z = OMe |
| 16 | H | H | H | OH | 4-BrC₆H₄ | H | H | H | | Z = Br |
| 17 | H | H | H | OH | 4-CF₃C₆H₄ | H | H | H | | Z = CF₃ |
| 18 | H | H | H | OH | 2-thienyl | H | H | H | | |
| 19 | H | Me | H | OH | Et | H | Me | H | Y¹ = H | Y² = Et |
| 20 | H | Me | H | OH | Pr | H | Me | H | | Y² = Pr |
| 21 | H | Me | H | OH | Bu | H | Me | H | | Y² = Bu |
| 22 | H | H | H | H | Ph | H | H | H | | |
| 23 | H | H | H | Me | Ph | H | H | H | Y¹ = Me; Y² = Ph | |

The products obtained in Examples 1-23 were identified and the results are shown below.

Example 1

Yield: 83%; scarlet red solid; m.p. 265-268° C.; $^1$H NMR (500 MHz, CDCl$_3$): δ 7.52-7.50 (m, 5H), 7.47-7.38 (m, 2H), 7.28-7.19 (m, 10H), 7.12-7.06 (m, 5H), 7.05-6.96 (m, 5H), 6.92-6.88 (m, 2H), 6.80 (td, J=8.0, 2.0 Hz, 1H), 6.50-6.49 (m, 2H); $^{13}$C NMR (125 MHz, CDCl$_3$): δ 150.0, 149.3, 140.5, 138.6, 137.8, 137.6, 136.9, 136.8, 135.6, 135.2, 134.6, 131.8, 131.7, 131.2, 130.9, 130.2, 130.0, 129.7, 128.5, 128.2, 127.9, 126.9, 126.7, 126.6, 126.5, 125.9, 125.5, 124.9, 123.2, 121.8, 118.9, 117.5; HRMS (FAB$^+$) m/z: MH$^+$ calculated for C$_{49}$H$_{32}$N$_2$: 648.2565.
Found: 648.2563; IR (KBr): 3054, 2929, 2337, 1342 cm$^{-1}$.

Example 2

Yield: 78%; orange solid; m.p. 294-297° C.; $^1$H NMR (400 MHz, CDCl$_3$): δ 7.51-7.45 (m, 5H), 7.26-7.17 (m, 8H), 7.07-6.95 (m, 11H) 6.93-6.86 (m, 3H), 6.77 (td, J=7.2, 1.2 Hz, 1H), 6.71 (s, 1H), 6.45 (d, J=7.2 Hz, 2H), 2.27 (s, 3H); $^{13}$C NMR (125 MHz, CDCl$_3$): δ 150.2, 149.3, 141.4, 140.7, 138.8, 138.0, 137.9, 137.4, 137.1, 136.9, 135.8, 135.2, 134.6, 131.9, 131.8, 131.3, 130.2, 130.1, 129.8, 128.5, 128.3, 128.2, 127.9, 127.8, 127.5, 127.0, 126.7, 126.6, 126.5, 125.8, 125.4, 124.9, 122.8, 120.4, 119.0, 118.8, 22.6; HRMS (EI$^+$) calculated for C$_{50}$H$_{34}$N$_2$: 662.2722. found: 662.2724; IR (KBr): 3054, 2931, 2337, 1342 cm$^{-1}$.

Example 3

Yield: 70%; orange solid; m.p. 325-328° C.; $^1$H NMR (500 MHz, CDCl$_3$): δ 7.53-7.42 (m, 5H), 7.26-7.18 (m, 8H), 7.13-7.02 (m, 10H), 6.99-6.98 (m, 3H), 6.97-6.86 (m, 2H), 6.78 (tt, J=8.5, 1.5 Hz, 1H), 6.47-6.44 (m, 2H), 1.16 (s, 9H); $^{13}$C NMR (125 MHz, CDCl$_3$): δ 154.1, 150.1, 149.1, 140.7, 138.7, 137.9, 137.5, 137.4, 137.1, 137.0, 135.5, 134.8, 134.6, 131.9, 131.7, 131.2, 130.3, 129.6, 128.6, 128.2, 128.1, 127.9, 127.8, 127.5, 127.0, 126.7, 126.6, 126.5, 126.4, 125.8, 125.3, 124.8, 123.3, 120.3, 119.2, 116.1, 115.0, 35.4, 31.0; HRMS (EI$^+$) calculated for C$_{53}$H$_{40}$N$_2$: 704.3191. found: 704.3188; IR (KBr): 3054, 2931, 2337 1319 cm$^{-1}$.

Example 4

Yield: 66%, orange solid; m.p. 289-293° C.; $^1$H NMR (400 MHz, CDCl$_3$): δ 7.50-7.42 (m, 5H), 7.27-7.16 (m, 8H), 7.10-7.00 (m, 9H), 6.98-6.86 (m, 4H), 6.79 (td, J=8.4, 2.0 Hz, 1H), 6.60 (d, J=2.4 Hz, 1H), 6.46 (d, J=2.4 Hz, 1H), 6.45 (d, J=7.2 Hz, 2H), 3.64 (s, 3H); $^{13}$C NMR (125 MHz, CDCl$_3$): δ 161.9, 150.6, 148.9, 140.7, 139.8, 138.6, 138.0, 137.4, 137.3, 136.9, 136.4, 134.6, 131.8, 131.7, 131.1, 130.2, 130.0, 129.8, 128.6, 128.3, 128.0, 127.8, 127.3, 127.0, 126.7, 126.5, 125.3, 124.9, 122.8, 118.4, 117.7, 107.1, 100.1, 55.1; HRMS (EI$^+$) calculated for $C_{50}H_{34}N_2O$: 678.2671. found: 678.2671; IR (KBr): 3054, 2923, 2337, 1350, 1123 cm$^{-1}$.

Example 5

Yield: 86%; scarlet red solid; m.p. 196-200° C.; $^1$H NMR (500 MHz, CDCl$_3$): δ 7.55-7.46 (m, 5H), 7.28-7.19 (m, 9H), 7.14-6.98 (m, 11H), 6.93-6.90 (m, 2H), 6.84-6.80 (m, 1H), 6.59 (d, J=10.0, 2.5 Hz, 1H), 6.48-6.46 (m, 2H); $^{13}$C NMR (125 MHz, CDCl$_3$): δ 164.9 (d$_{C-F}$, J=246.1 Hz), 151.0, 148.9, 140.1 (d$_{C-F}$, J=11.0 Hz), 138.5 (d$_{C-F}$, J=11.0 Hz), 138.2, 137.4, 137.2, 136.9, 136.7, 134.5, 131.7, 131.6, 131.0, 130.1, 130.0, 128.6, 128.4, 128.2, 127.8, 127.0, 126.9, 126.8, 126.6, 126.0, 125.9, 125.0, 123.1 (d, J=4.5 Hz), 119.0, 118.3, 105.7 (d$_{C-F}$, J=27.6 Hz), 103.5 (d$_{C-F}$, J=24.2 Hz); HRMS (EI$^+$) calculated for $C_{49}H_{31}FN_2$: 666.2471. found: 666.2460; IR (KBr): 3054, 2932, 1350, 1126 cm$^{-1}$.

Example 6

Yield: 75%; orange solid; m.p. 284-287° C.; $^1$H NMR (400 MHz, CDCl$_3$): δ 7.55-7.47 (m, 5H), 7.27-7.19 (m, 9H), 7.15-6.90 (m, 11H), 6.89 (t, J=7.6 Hz, 2H), 6.86-6.82 (m, 2H), 6.46 (d, J=8.4 Hz, 2H); $^{13}$C NMR (100 MHz, CDCl$_3$): δ 151.2, 149.1, 140.2, 139.0, 138.1, 138.0, 137.3, 137.2, 137.0, 136.8 136.7, 134.5, 131.8, 131.8, 131.6, 131.1, 130.2, 130.1, 128.7, 128.6, 128.5, 128.3, 127.9, 127.1, 126.8, 126.7, 126.1, 126.0, 125.1, 122.6, 120.1, 118.0, 117.7, 117.3; HRMS (EI$^+$) calculated for $C_{49}H_{31}ClN_2$: 682.2176. found: 682.2174; IR (KBr): 3054, 2923, 1342, 1126, 995 cm$^{-1}$.

Example 7

Yield: 72%; scarlet red solid; m.p. 310-312° C.; $^1$H NMR (400 MHz, CDCl$_3$): δ 7.55-7.47 (m, 5H), 7.29-7.17 (m, 9H), 7.12-6.94 (m, 12H), 6.89 (t, J=7.2 Hz, 2H), 6.81 (td, J=6.4, 2.0 Hz, 1H), 6.45 (d, J=8.4 Hz, 2H); $^{13}$C NMR (125 MHz, CDCl$_3$): δ 165.9, 163.9, 151.0, 149.0, 140.2, 140.1, 138.5, 138.4, 138.2, 137.4, 137.2, 137.0, 136.7, 134.5, 131.7, 131.6, 131.0, 130.2, 130.0, 128.6, 128.4, 128.2, 127.8, 127.0, 126.9, 126.8, 126.6, 126.0, 125.9, 125.0, 123.1, 119.0, 118.3, 105.6, 103.6, 103.4; HRMS (EI$^+$) calculated for $C_{49}H_{31}BrN_2$: 726.1671.
Found: 726.1640; IR (KBr): 3054, 2931, 1565, 1334, 956 cm$^{-1}$.

Example 8

Yield: 78%; orange solid; m.p. 236-240° C.; $^1$H NMR (500 MHz, CDCl$_3$): δ 7.55-7.46 (m, 5H), 7.28-7.16 (m, 9H), 7.14-6.98 (m, 12H), 6.92-6.89 (m, 2H), 6.81 (td, J=6.4, 2.0 Hz, 1H), 6.47-6.46 (m, 2H); $^{13}$C NMR (125 MHz, CDCl$_3$): δ 151.0, 149.2, 140.2, 139.1, 138.0, 137.1, 136.8, 136.6, 134.4, 131.7, 131.6, 131.1, 130.1, 130.0, 128.6, 128.5, 128.3, 127.8, 127.2, 127.1, 127.0, 126.8, 126.7, 126.0, 125.7, 125.0, 121.9, 120.5, 117.6, 99.8; HRMS (EI$^+$) calculated for $C_{49}H_{31}IN_2$: 774.1532. found: 774.1526; IR (KBr): 3054, 2923, 1560, 1342, 950 cm$^{-1}$.

Example 9

Yield: 63%; orange solid; m.p. 277-279° C.; $^1$H NMR (400 MHz, CDCl$_3$): δ 7.55-7.48 (m, 5H), 7.41 (s, 1H), 7.29-7.20 (m, 8H), 7.15-6.98 (m, 12H), 6.91 (t, J=8.0 Hz, 2H), 6.82 (td, J=8.4, 2.4 Hz, 1H), 6.47 (d, J=8.4 Hz, 2H); $^{13}$C NMR (100 MHz, CDCl$_3$): δ 151.3, 149.0, 140.0, 137.9, 137.6, 137.0, 136.9, 136.6, 136.5, 134.4, 132.9, 132.6, 132.2, 131.7, 131.5, 131.0, 130.8, 130.1, 129.9, 129.0, 128.7, 128.6, 128.5, 128.4, 127.9, 127.4, 127.2, 127.1, 126.8, 126.7, 126.2, 126.1, 125.1, 123.7, 122.4, 118.5, 115.5, 112.9; HRMS (EI$^+$) calculated for $C_{50}H_{31}F_3N_2$: 716.2439. found: 716.2443; IR (KBr): 3062, 2923, 2337, 1319 cm$^{-1}$.

Example 10

Yield: 68%; red solid; m.p. 259-261° C.; $^1$H NMR (400 MHz, CDCl$_3$): δ 7.54-7.42 (m, 5H), 7.26-7.14 (m, 8H), 7.13-6.94 (m, 11H), 6.87 (d, J=7.2 Hz, 2H), 6.78 (td, J=8.4, 1.6 Hz, 1H), 6.44 (d, J=8.4 Hz, 2H), 6.38 (dm, J=2.0 Hz, 1H), 6.34 (dm, J=2.0 Hz, 1H), 2.79 (s, 6H); $^{13}$C NMR (125 MHz, CDCl$_3$): δ 152.1, 150.2, 148.9, 141.1, 149.3, 139.0, 138.6, 137.5, 137.1, 136.4, 136.0, 134.7, 131.7, 131.3, 130.2, 130.0, 129.6, 128.5, 128.2, 128.0, 127.8, 127.4, 126.9, 126.6, 126.3, 126.2, 125.6, 124.7, 121.9, 118.7, 115.4, 104.7, 99.2, 40.1; HRMS (EI$^+$) calculated for $C_{51}H_{37}N_3$: 691.2987. found: 691.2998; IR (KBr): 3054, 2923, 2337, 1357 cm$^{-1}$.

Example 11

Yield: 81%; red solid; m.p. 284-288° C.; $^1$H NMR (400 MHz, CDCl$_3$): δ 7.58-7.40 (m, 6H), 7.37-7.21 (m, 12H), 7.15-6.97 (m, 12H), 6.91 (td, J=7.6, 2.0 Hz, 2H), 6.81 (td, J=6.8, 1.6 Hz, 2H), 6.44 (d, J=8.4 Hz, 2H); $^{13}$C NMR (100 MHz, CDCl$_3$): δ 150.5, 149.3, 143.8, 141.4, 140.6, 138.6, 138.0, 137.7, 137.0, 136.9, 135.8, 134.6, 132.5, 131.8, 131.7, 131.2, 130.2, 130.1, 129.9, 129.6, 129.1, 129.0, 128.7, 128.6, 128.3, 128.0, 127.8, 127.7, 127.6, 127.5, 127.4, 127.2, 127.0, 126.8, 126.7, 123.4, 121.0, 119.0, 117.4, 116.9; HRMS (EI$^+$) calculated for $C_{55}H_{36}N_2$: 724.2878. found: 724.2879; IR (KBr): 3054, 2932, 2337, 1343 cm$^{-1}$.

Example 12

Yield: 81%; scarlet red solid; m.p. 300-304° C.; $^1$H NMR (400 MHz, CDCl$_3$): δ 7.46-7.36 (m, 5H), 7.23-7.17 (m, 6H), 7.07-6.96 (m, 11H), 6.91 (td, J=7.2, 1.6 Hz, 2H), 6.84 (t, J=7.6 Hz, 2H), 6.60 (d, J=8.0 Hz, 1H), 6.35 (d, J=8.4 Hz, 2H), 3.83 (s, 3H), 3.28 (s, 3H) 3.20 (s, 3H); $^{13}$C NMR (100 MHz, CDCl$_3$): δ 151.0, 150.7, 149.1, 146.3, 146.0, 140.8, 140.3, 140.2, 137.3, 136.9, 136.8, 134.9, 134.4, 131.9, 131.4, 131.1, 131.0, 130.7, 130.1, 130.0, 129.9, 129.5, 129.1, 129.0, 128.8, 128.7, 126.8, 128.4, 128.0, 127.8, 127.5, 127.3, 127.0, 126.9, 126.7, 126.6, 126.3, 125.6, 125.3, 124.9, 122.9, 121.4, 121.0, 117.3, 61.2, 60.7, 60.4; HRMS (EI$^+$) calculated for $C_{52}H_{38}N_2O_3$: 738.2882. found: 738.2886; IR (KBr): 3054, 2932, 2337, 1343, 1203 cm$^{-1}$.

Example 13

Yield: 70% (a total yield of two isomers); red solid; m.p. 196-200° C.; $^1$H NMR (400 MHz, CDCl$_3$): δ 7.50-7.39 (m, 11H), 7.37-7.24 (m, 12H), 7.19-7.01 (m, 12H), 6.99-6.89 (m, 10H), 6.82-6.74 (m, 3H), 6.49 (d, J=8.4 Hz, 2H), 6.36 (d, J=8.8 Hz, 2H), 3.38 (s, 3H), 3.37 (s, 2H); $^{13}$C NMR (100 MHz, CDCl$_3$): δ 151.5, 150.3, 149.8, 149.3, 148.1, 140.8, 140.7, 140.5, 138.7, 137.7, 137.5, 137.3, 137.1, 137.0, 136.9, 136.6, 135.0, 134.6, 132.3, 131.9, 131.7, 131.2, 130.9, 130.3, 130.2, 129.7, 129.0, 128.8, 128.6, 128.5, 128.4, 128.2, 128.1, 127.8, 127.7, 127.6, 127.5, 127.2, 127.0, 126.9, 126.8, 126.7, 126.6, 126.5, 126.4, 126.1, 125.8, 125.6, 125.4, 125.1, 124.7, 124.5, 124.3, 123.9, 119.6, 118.6, 116.7, 112.8; HRMS (EI$^+$) calculated for $C_{50}H_{34}N_2O$: 678.2671. found: 678.2682; IR (KBr): 3054, 2929, 2336, 1342, 1205 cm$^{-1}$.

Example 14

Yield: 76%; orange solid; m.p. 246-250° C.; $^1$H NMR (400 MHz, CDCl$_3$): δ 7.36 (t, J=7.6 Hz, 2H), 7.30 (t, J=7.6 Hz, 2H), 7.13-7.07 (m, 7H), 6.95 (d, J=8.0 Hz, 4H), 6.90-6.79 (m, 6H), 6.72 (d, J=8.0 Hz, 2H), 6.62 (d, J=8.0 Hz, 1H), 6.40 (d, J=8.0 Hz, 2H), 2.45 (s, 3H), 2.34 (s, 3H), 2.31 (s, 3H), 2.21 (s, 3H), 2.16 (s, 3H), 2.13 (s, 3H); $^{13}$C NMR (100 MHz, CDCl$_3$): δ 149.8, 149.4, 137.9, 137.4, 137.3, 136.0, 135.9, 135.8, 135.6, 135.1, 134.8, 134.2, 134.1, 131.7, 131.6, 131.0, 130.6, 130.4, 130.1, 129.0, 128.5, 128.4, 127.6, 127.4, 126.9, 125.1, 125.0, 122.6, 121.5, 118.5, 117.9, 116.9, 21.4, 21.3, 21.2, 21.0; HRMS (EI$^+$) calculated for $C_{55}H_{44}N_2$: 732.3504. found: 732.3501 IR (KBr): 3054, 2923, 2337, 1342 cm$^{-1}$.

Example 15

Yield: 80%; orange solid; m.p. 296-299° C.; $^1$H NMR (400 MHz, CDCl$_3$): δ 7.39-7.34 (m, 3H), 7.15-6.98 (m, 9H), 6.94 (d, J=8.4 Hz, 1H), 6.83-6.80 (m, 5H), 6.59-6.52 (m, 5H), 6.46 (d, J=8.4 Hz, 2H), 6.40 (d, J=8.4 Hz, 1H), 3.88 (s, 3H), 3.79 (s, 3H), 3.78 (s, 3H), 3.68 (s, 3H), 3.66 (s, 3H), 3.60 (s, 3H); $^{13}$C NMR (125 MHz, CDCl$_3$): δ 159.1, 159.0, 158.2, 158.1, 157.9, 149.5, 149.3, 138.0, 137.8, 136.8, 135.7, 133.4, 132.8, 132.7, 132.2, 131.5, 130.9, 130.7, 130.4, 130.0, 129.6, 129.3, 122.0, 121.1, 120.9, 118.2, 116.7, 115.2, 113.8, 113.3, 112.4, 112.2, 109.0, 55.2, 55.1, 55.0, 54.9; HRMS (EI$^+$) calculated for $C_{55}H_{44}N_2O_6$: 828.3199. found: 828.3204; IR (KBr): 3054, 2923, 2337, 1342 cm$^{-1}$.

Example 16

Yield: 73%; red solid; m.p. 254-258° C.; $^1$H NMR (400 MHz, CDCl$_3$): δ 7.64 (t, J=8.4 Hz, 2H), 7.45-7.40 (m, 6H), 7.33 (d, J=8.4 Hz, 2H), 7.14-7.09 (m, 6H), 6.99 (dd, J=8.8, 2.8 Hz, 4H), 6.92 (d, J=8.0 Hz, 2H), 6.88-6.79 (m, 2H), 6.33 (d, J=8.4 Hz, 2H); $^{13}$C NMR (100 MHz, CDCl$_3$): δ 148.8, 148.7, 138.7, 137.7, 137.3, 136.8, 135.9, 135.8, 135.3, 134.6, 134.4, 133.3, 133.2, 133.1, 132.7, 131.8, 131.7, 131.6, 131.5, 131.3, 131.0, 130.4, 130.3, 130.0, 129.6, 127.3, 125.6, 123.4, 122.8, 122.4, 121.7, 121.6, 121.4, 121.3, 120.9, 119.5, 118.4, 118.0; HRMS (EI$^+$) m/z: MH$^+$ calculated for $C_{49}H_{26}Br_6N_2$: 1115.7196. found: 1122.7220; IR (KBr): 3054, 2923, 2337, 1342 cm$^{-1}$.

Example 17

Yield: 68%; orange solid; m.p. 282-284° C.; $^1$H NMR (400 MHz, CDCl$_3$): δ 7.83 (d, J=8.4 Hz, 2H), 7.64 (d, J=8.0 Hz, 2H), 7.64 (dd, J=8.0, 2.0 Hz, 4H), 7.50 (t, J=8.0 Hz, 1H), 7.28 (d, J=8.0 Hz, 2H), 7.24-7.10 (m, 11H), 7.02 (d, J=8.4 Hz, 1H), 6.89 (d, J=7.6 Hz, 1H), 6.53 (d, J=8.0 Hz, 2H); $^{13}$C NMR (100 MHz, CDCl$_3$): δ 148.8, 148.6, 142.9, 141.6, 140.4, 139.9, 138.8, 138.1, 137.3, 134.3, 134.2, 132.0, 131.9, 131.4, 131.1, 130.9, 130.8, 130.3, 130.2, 129.9, 129.8, 129.6, 129.5, 129.4, 129.2, 127.3, 127.2, 125.8, 125.7, 125.5, 125.3, 124.2, 124.1, 123.5, 123.4, 123.3, 122.6, 122.1, 121.6, 121.5, 120.2, 119.8, 118.9; HRMS (EI$^+$) m/z: MH$^+$ calculated for $C_{55}H_{26}F_{18}N_2$: 1056.1809. found: 1057.2000, IR (KBr): 3054, 2923, 2337, 1342 cm$^{-1}$.

Example 18

Yield: 60%; scarlet red solid; m.p. 226-230° C.; $^1$H NMR (400 MHz, CDCl$_3$): δ 7.66 (d, J=5.2 Hz, 1H), 7.50 (d, J=5.2 Hz, 1H), 7.42 (t, J=8.4 Hz, 1H), 7.32 (d, J=5.2 Hz, 1H), 7.28 (t, J=3.2 Hz, 1H) 7.20-7.17 (m, 3H), 7.13-7.04 (m, 4H), 7.01-6.98 (m, 2H), 6.89 (d, J=3.6 Hz, 1H), 6.78-6.76 (m, 2H), 6.73 (t, J=4.0 Hz, 1H), 6.65 (t, J=4.0 Hz, 1H), 6.56 (d, J=3.6 Hz, 1H); $^{13}$C NMR (125 MHz, CDCl$_3$): δ 150.7, 144.7, 143.8, 140.0, 139.2, 138.4, 137.6, 137.5, 137.0, 135.8, 135.5, 132.6, 131.6, 130.8, 130.2, 129.3, 129.1, 129.0, 128.9, 128.4, 127.9, 127.8, 127.3, 126.6, 126.0, 125.4, 124.1, 119.4, 118.4, 118.2, 116.7, 114.1, 105.5; HRMS (EI$^+$) calculated for $C_{37}H_{20}N_2S_6$: 683.9951. found: 683.9952; IR (KBr): 3100, 2923, 2337, 1357 cm$^{-1}$.

Example 19

Yield: 72%; yellow solid; m.p. 86-90° C.; $^1$H NMR (400 MHz, CDCl$_3$): δ 7.18 (s, 1H), 6.77 (s, 1H), 2.83-2.75 (m, 4H), 2.55-2.45 (m, 7H), 1.29-1.24 (m, 6H), 1.98-1.12 (m, 6H); $^{13}$C NMR (100 MHz, CDCl$_3$): δ 157.2, 154.4, 152.9, 142.0, 138.5, 133.1, 122.3, 117.3, 115.0, 113.9, 112.9, 28.1, 24.0, 22.9, 20.4, 19.3, 14.6, 14.1, 13.0, 12.7; HRMS (ESI$^+$) calculated for $[C_{20}H_{26}N_2+H]^+$: 295.2174. found: 295.2176; IR (KBr): 2954, 2923, 1643, 1234 cm$^{-1}$.

Example 20

Yield: 80%; yellow solid; m.p. 126-130° C.; $^1$H NMR (400 MHz, CDCl$_3$): δ 7.16 (s, 1H), 6.75 (s, 1H), 2.77-2.71 (m, 4H), 2.51-2.41 (m, 7H), 1.76-1.69 (m, 4H), 1.60-1.53 (m, 4H), 1.05-0.95 (m, 12H); $^{13}$C NMR (100 MHz, CDCl$_3$): δ 157.1, 153.5, 152.0, 141.9, 138.7, 133.3, 121.3, 117.5, 115.2, 113.8, 112.0, 37.9, 32.7, 29.5, 28.3, 23.5, 22.9, 21.4, 21.2, 14.4, 14.3, 14.2, 13.8; HRMS (ESI$^+$) calculated for $[C_{24}H_{34}N_2+H]^+$: 351.2800. found: 351.2805; IR (KBr): 2952, 2923, 1645, 1234 cm$^{-1}$.

Example 21

Yield: 88%; yellow solid; m.p. 110-115° C.; $^1$H NMR (400 MHz, CDCl$_3$): δ 7.16 (s, 1H), 6.75 (s, 1H), 2.77-2.71 (m, 4H), 2.51-2.41 (m, 7H), 1.76-1.69 (m, 4H), 1.60-1.53 (m, 4H), 1.05-0.95 (m, 12H); $^{13}$C NMR (100 MHz, CDCl$_3$): δ 157.1, 153.6, 152.1, 141.8, 138.7, 133.4, 121.3, 117.4, 115.2, 115.1, 113.8, 111.9, 34.9, 32.5, 31.8, 30.6, 30.4, 30.0, 27.1, 26.0, 23.1, 23.0, 22.9, 22.8, 22.6, 14.1, 14.0, 13.9, 13.8; HRMS (ESI$^+$) calculated for $[C_{28}H_{42}N_2+H]^+$: 407.3426. found: 407.3424; IR (KBr): 2954, 2923, 1643, 1234 cm$^{-1}$.

Example 22

Yield: 83%; scarlet red solid; m.p. 265-268° C.; $^1$H NMR (500 MHz, CDCl$_3$): δ 7.52-7.50 (m, 5H), 7.47-7.38 (m, 2H), 7.28-7.19 (m, 10H), 7.12-7.06 (m, 5H), 7.05-6.96 (m, 5H), 6.92-6.88 (m, 2H), 6.80 (td, J=8.0, 2.0 Hz, 1H), 6.50-6.49 (m, 2H); $^{13}$C NMR (125 MHz, CDCl$_3$): δ 150.0, 149.3, 140.5, 138.6, 137.8, 137.6, 136.9, 136.8, 135.6, 135.2, 134.6, 131.8, 131.7, 131.2, 130.9, 130.2, 130.0, 129.7, 128.5, 128.2, 127.9, 126.9, 126.7, 126.6, 126.5, 125.9, 125.5, 124.9, 123.2, 121.8, 118.9, 117.5; HRMS (FAB$^+$) m/z: MH$^+$ calculated for $C_{49}H_{32}N_2$: 648.2565.

Found: 648.2563; IR (KBr): 3054, 2929, 2337, 1342 cm$^{-1}$.

Example 23

Yield: 68%; yellow solid; m.p. 265-268° C.; $^1$H NMR (400 MHz, CDCl$_3$): δ 7.41-7.30 (m, 5H), 7.29-7.21 (m, 8H), 7.20-7.14 (m, 6H), 7.08-7.06 (m, 2H), 6.78 (s, 1H), 6.34 (s, 1H), 3.36 (s, 3H); $^{13}$C NMR (100 MHz, CDCl$_3$): δ 152.1, 149.9, 143.0, 141.7, 141.4, 138.8, 138.2, 137.2, 136.5, 135.6, 131.4, 131.3, 130.1, 130.0, 129.8, 129.0, 128.5, 128.3, 128.1, 127.9, 127.8, 127.4, 127.2, 126.8, 126.6, 126.5, 126.4, 125.3, 120.9, 118.8, 118.3, 117.4, 116.5, 35.3; HRMS (FAB$^+$) calculated for $C_{36}H_{26}N_2$: 486.2096.

Found: 486.2099; IR (KBr): 3054, 2929, 2337, 1342 cm$^{-1}$.

Influence of Catalyst, Oxidant and Solvent

Examples 1a-1i and Comparative Example

Example 1 was repeated using (Z)-N-hydroxybenzamidine, diphenylacetylene, and the catalysts, the oxidants and the solvents shown in Table 2. The results are also shown in Table 2.

TABLE 2

| Ex. | Catalyst | Oxidant | Solvent | Yield (%) |
|---|---|---|---|---|
| 1a | [Cp*Rh(CH$_3$CN)$_3$](SbF$_6$)$_2$ | Cu(OAc)$_2$ | DMF | 70 |
| 1b | [Cp*Rh(CH$_3$CN)$_3$](SbF$_6$)$_2$ | Cu(OAc)$_2$ | o-xylene | 64 |
| 1c | [Cp*Rh(CH$_3$CN)$_3$](SbF$_6$)$_2$ | Cu(OAc)$_2$ | dichloroethane | 58 |
| 1d | [Cp*Rh(CH$_3$CN)$_3$](SbF$_6$)$_2$ | Cu(OAc)$_2$ | acetonitrile | 45 |
| 1e | [Cp*Rh(CH$_3$CN)$_3$](SbF$_6$)$_2$ | Cu(OAc)$_2$ | acetic acid | 50 |
| 1f | [Cp*Rh(CH$_3$CN)$_3$](SbF$_6$)$_2$ | Cu(OAc)$_2$·H$_2$O | t-amylOH | 62 |
| 1g | [Cp*Rh(CH$_3$CN)$_3$](SbF$_6$)$_2$ | Cu(OTf)$_2$ | t-amylOH | 15 |
| 1h | [RhCp*Cl$_2$]$_2$(3 mol %) | Cu(OAc)$_2$ | t-amylOH | 68 |
| 1i | [RuCl$_2$(p-cymene)]$_2$ | Cu(OAc)$_2$ | t-amylOH | 43 |
| Comp. Ex. | Pd(OAc)$_2$ | Cu(OAc)$_2$ | t-amylOH | 0 |

As evidenced by the yield data shown in Table 2, the 1,9-diazaphenalene derivative obtained in Example 1 may also be obtained using a rhodium-containing complex or a ruthenium-containing complex as a catalyst and using various solvents. However, the 1,9-diazaphenalene derivative obtained in Example 1 may not be obtained using a palladium-containing complex as a catalyst.

Synthesis (II) of 1,9-Diazaphenalene Derivative

Examples 24-37

0.3 mmol of a benzonitrile compound of formula (IV), 1.5 mmol of an amine compound of formula (V), 0.66 mmole of an alkyne compound of formula (II), 4.0 mol % of [Cp*Rh(CH$_3$CN)$_3$](SbF$_6$)$_2$ (Cp* represents pentamethylcyclopentadienyl), and 1.35 mmol (4.5 equivalents) of copper (II) acetate were added into a sealed tube. The sealed tube was then evacuated and purged with nitrogen gas three times. 3 ml of 2-methyl-2-butanol was subsequently added into the sealed tube via a syringe under a nitrogen atmosphere to obtain a reaction mixture, which was stirred at 130° C. for 18 hours. The mixture was then cooled and diluted with CH$_2$Cl$_2$ (10 ml), followed by filtration through a Celite pad. The Celite pad was washed with CH$_2$Cl$_2$ (50 ml) to obtain a filtrate. The filtrate was concentrated in vacuo and the residue was purified by a silica gel column using hexane-EtOAc (5-15%) as eluent to give a product of formula (III).

The definitions of $R^1$, $R^2$, $R^3$, X, R, $Y^1$, and $Y^2$ in formulae (I), (II), and (III) in Examples 24-37 are listed in Table 3.

TABLE 3

| | Formula (IV) | | | Formula (V) | Formulae (II) and (III) | Formula (III) | | | |
|---|---|---|---|---|---|---|---|---|---|
| Ex. | $R^1$ | $R^2$ | $R^3$ | X | R | $R^1$ | $R^2$ | $R^3$ | $Y^1$ and $Y^2$ |
| 24 | H | H | H | Me | Ph | H | H | H | $Y^1$ = Me; $Y^2$ = Ph |
| 25 | H | Me | H | Me | Ph | H | Me | H | |
| 26 | H | tBu | H | Me | Ph | H | tBu | H | |
| 27 | H | F | H | Me | Ph | H | F | H | |
| 28 | H | Cl | H | Me | Ph | H | Cl | H | |
| 29 | H | Br | H | Me | Ph | H | Br | H | |
| 30 | H | CF$_3$ | H | Me | Ph | H | CF$_3$ | H | |
| 31 | H | N(Me)$_2$ | H | Me | Ph | H | N(Me)$_2$ | H | |
| 32 | H | Ph | H | Me | Ph | H | Ph | H | |
| 33 | H | CO$_2$Me | H | Me | Ph | H | CO$_2$Me | H | |
| 34 | H | COMe | H | Me | Ph | H | COMe | H | |
| 35 | H | CHO | H | Me | Ph | H | CHO | H | |
| 36 | H | H | H | Pr | Ph | H | H | H | $Y^1$ = Pr; $Y^2$ = Ph |

TABLE 3-continued

| | Formula (IV) | | | Formula (V) | Formulae (II) and (III) | Formula (III) | | | |
|---|---|---|---|---|---|---|---|---|---|
| Ex. | $R^1$ | $R^2$ | $R^3$ | X | R | $R^1$ | $R^2$ | $R^3$ | $Y^1$ and $Y^2$ |
| 37 | H | H | H | H | Ph | H | H | H | (structure shown) |

The products obtained in Examples 24-37 were identified and the results are shown below.

Example 24

Yield: 68%; yellow solid; m.p. 265-268° C.; $^1$H NMR (400 MHz, CDCl$_3$): δ 7.41-7.30 (m, 5H), 7.29-7.21 (m, 8H), 7.20-7.14 (m, 6H), 7.08-7.06 (m, 2H), 6.78 (s, 1H), 6.34 (s, 1H), 3.36 (s, 3H); $^{13}$C NMR (100 MHz, CDCl$_3$): δ 152.1, 149.9, 143.0, 141.7, 141.4, 138.8, 138.2, 137.2, 136.5, 135.6, 131.4, 131.3, 130.1, 130.0, 129.8, 129.0, 128.5, 128.3, 128.1, 127.9, 127.8, 127.4, 127.2, 126.8, 126.6, 126.5, 126.4, 125.3, 120.9, 118.8, 118.3, 117.4, 116.5, 35.3; HRMS (FAB$^+$) calculated for $C_{36}H_{26}N_2$: 486.2096. Found: 486.2099; IR (KBr): 3054, 2929, 2337, 1342 cm$^{-1}$.

Example 25

Yield: 74%; yellow solid; m.p. 251-255° C.; $^1$H NMR (400 MHz, CDCl$_3$): δ 7.41-7.30 (m, 5H), 7.29-7.21 (m, 8H), 7.20-7.14 (m, 5H), 7.08-7.06 (m, 2H), 6.78 (s, 1H), 6.34 (s, 1H), 3.37 (s, 3H), 2.17 (s, 3H); $^{13}$C NMR (100 MHz, CDCl$_3$): δ 152.1, 149.9, 143.0, 141.7, 141.4 138.8, 138.2, 137.2, 136.5, 135.6, 131.4, 131.3, 130.1, 130.0, 129.8, 129.0, 128.5, 128.3, 128.1, 127.9, 127.8, 127.4, 127.2, 126.8, 126.6, 126.5, 126.4, 125.3, 120.9, 118.8, 118.3, 117.4, 116.5, 35.1, 22.4; HRMS (EI$^+$) calculated for $C_{37}H_{28}N$: 500.2252. found: 500.2250; IR (KBr): 3054, 2931, 2337, 1342 cm$^{-1}$.

Example 26

Yield: 80%; yellow solid; m.p. 276-280° C.; $^1$H NMR (400 MHz, CDCl$_3$): δ 7.57 (d, J=6.4 Hz, 1H), 7.49-7.31 (m, 5H), 7.29-7.14 (m, 12H), 7.08-7.06 (m, 2H), 6.80 (s, 1H), 6.57 (s, 1H), 3.34 (s, 3H), 1.16 (s, 9H); $^{13}$C NMR (100 MHz, CDCl$_3$): δ 154.2, 152.0, 149.8, 142.7, 141.7, 141.4 138.8, 138.2, 137.2, 136.5, 135.6, 131.4, 131.3, 130.1, 130.0, 129.8, 129.0, 128.5, 128.3, 128.1, 127.9, 127.8, 127.4, 127.2, 126.8, 126.6, 126.5, 126.4, 125.3, 120.9, 118.8, 118.3, 117.4, 116.5, 35.4, 31.0; HRMS (EI$^+$) calculated for $C_{40}H_{34}N_2$: 542.2722. found: 542.2724; IR (KBr): 3054, 2931, 2337, 1319 cm$^{-1}$.

Example 27

Yield: 77%; yellow solid; m.p. 176-180° C.; $^1$H NMR (400 MHz, CDCl$_3$): δ 7.53 (t, J=7.6 Hz, 2H), 7.46-7.32 (m, 4H), 7.28-7.19 (m, 9H), 7.08 (dd, J=7.6, 0.8 Hz, 1H), 6.97-6.88 (m, 4H), 6.67 (dd, J=8.0, 2.4 Hz, 1H), 6.23 (dd, J=8.0, 2.4 Hz, 1H), 3.43 (s, 3H); $^{13}$C NMR (100 MHz, CDCl$_3$) δ 164.9 ($d_{C-F}$, J=244.8 Hz), 151.5, 150.9, 144.1, 141.9, 141.3, 139.9, 139.8, 138.2, 136.6, 135.1, 134.8, 132.6, 131.9, 131.3, 130.1, 130.0, 129.8, 129.5, 128.9, 128.7, 128.5, 128.1, 127.9, 127.8, 127.4, 127.2, 126.9, 126.8, 126.5, 126.3, 125.5, 118.3, 105.7 ($d_{C-F}$, J=27.6 Hz), 103.5 ($d_{C-F}$, J=24.2 Hz), 35.3; HRMS (EI$^+$) calculated for $C_{36}H_{25}FN_2$: 504.2002. found: 504.2010; IR (KBr): 3054, 2932, 1350, 1126 cm$^{-1}$.

Example 28

Yield: 71%; yellow solid; m.p. 234-237° C.; $^1$H NMR (400 MHz, CDCl$_3$): δ 7.55-7.47 (m, 3H), 7.43-7.33 (m, 4H), 7.32-7.16 (m, 11H), 7.12 (d, J=7.6 Hz, 2H), 7.02 (s, 1H), 6.53 (s, 1H), 3.43 (s, 3H); $^{13}$C NMR (100 MHz, CDCl$_3$): δ 151.6, 151.0, 144.1, 141.1, 140.4, 138.4, 138.0, 137.9, 136.3, 135.0, 134.7, 131.3, 131.2, 130.0, 129.9, 129.8, 129.7, 128.9, 128.7, 128.5, 128.3, 128.2, 128.1, 127.2, 126.9, 126.8, 120.7, 118.7, 117.9, 116.3, 114.9, 35.3; HRMS (EI$^+$) calculated for $C_{36}H_{25}ClN_2$: 520.1706. found: 520.1709; IR (KBr): 3054, 2923, 1342, 1126, 995 cm$^{-1}$.

Example 29

Yield: 68%; yellow solid; m.p. 210-212° C.; $^1$H NMR (400 MHz, CDCl$_3$): δ 7.65 (t, J=7.6 Hz, 1H), 7.49-7.25 (m, 5H), 7.23-7.11 (m, 12H), 7.08 (dd, J=8.4 Hz, 2H), 6.67 (d, J=8.0 Hz, 1H), 6.23 (dd, J=8.0 Hz, J=2.4 Hz, 1H), 3.44 (s, 3H); $^{13}$C NMR (100 MHz, CDCl$_3$): δ 152.2, 149.7, 142.8, 141.5, 138.6, 137.1, 136.5, 135.4, 134.7, 131.3, 131.2, 130.0, 129.9, 129.8, 129.6, 128.9, 128.5, 128.3, 128.0, 127.7, 127.2, 126.8, 126.7, 126.5, 121.2, 120.4, 118.5, 117.3, 115.2, 35.2; HRMS (EI$^+$) calculated for $C_{36}H_{25}BrN_2$: 564.1201. found: 564.1209; IR (KBr): 3054, 2931, 1565, 1334, 956 cm$^{-1}$.

Example 30

Yield: 78%; yellow solid; m.p. 278-282° C.; $^1$H NMR (400 MHz, CDCl$_3$): δ 7.47-7.35 (m, 5H), 7.30-7.25 (m, 8H), 7.24-7.21 (m, 5H), 7.19 (d, J=1.6 Hz, 1H), 7.13-7.11 (m, 2H), 6.70 (d, J=1.2 Hz, 1H), 3.46 (s, 3H); $^{13}$C NMR (100 MHz, CDCl$_3$): δ 151.7, 151.1, 144.2, 141.1, 139.1, 137.7, 136.2, 135.0, 133.0 (q, J=256.6 Hz), 131.3, 131.1, 131.0, 130.3, 130.1, 129.7, 128.9, 128.8, 128.6, 128.4, 128.2, 127.5, 127.3, 127.0, 126.9, 121.8, 121.4, 118.5, 113.8 (d, J=3.8 Hz), 110.6 (d, J=3.0 Hz), 35.4; HRMS (EI$^+$) calculated for $C_{37}H_{25}F_3N_2$: 554.1970. Found: 554.1972; IR (KBr): 3062, 2923, 2337, 1319 cm$^{-1}$.

Example 31

Yield: 72%; yellow solid; m.p. 252-256° C.; $^1$H NMR (400 MHz, CDCl$_3$): δ 7.40-7.30 (m, 5H), 7.29-7.20 (m, 8H), 7.20-7.14 (m, 5H), 7.08-7.04 (m, 2H), 6.77 (s, 1H), 6.33 (s, 1H), 3.37 (s, 3H), 2.79 (s, 6H); $^{13}$C NMR (100 MHz, CDCl$_3$): δ 152.1, 149.9, 143.0, 141.7, 141.4 138.8, 138.2, 137.2, 136.5, 135.6, 131.4, 131.3, 130.1, 130.0, 129.8, 129.0, 128.5, 128.3, 128.1, 127.9, 127.8, 127.4, 127.2, 126.8, 126.6, 126.5, 126.4, 125.3, 120.9, 118.8, 118.3, 117.4, 116.5, 35.1, 22.4; HRMS (EI$^+$) calculated for C$_{38}$H$_{31}$N$_3$: 529.2518. found: 529.2521; IR (KBr): 3054, 2932, 2333, 1342 cm$^{-1}$.

Example 32

Yield: 82%; yellow solid; m.p. 271-274° C.; $^1$H NMR (400 MHz, CDCl$_3$): δ 7.41-7.30 (m, 5H), 7.29-7.21 (m, 8H), 7.20-7.10 (m, 10H), 7.08-7.06 (m, 2H), 6.78 (s, 1H), 6.34 (s, 1H), 3.43 (s, 3H); $^{13}$C NMR (100 MHz, CDCl$_3$): δ 152.1, 149.9, 143.0, 141.7, 141.4, 138.8, 138.2, 137.2, 136.5, 135.6, 135.2, 134.6, 131.4, 131.3, 130.1, 130.0, 129.8, 129.0, 128.5, 128.3, 128.1, 127.9, 127.8, 127.4, 127.2, 126.8, 126.6, 126.5, 126.4, 125.3, 120.9, 118.8, 118.3, 117.4, 116.5, 35.3; HRMS (EI$^+$) calculated for C$_{42}$H$_{30}$N$_2$: 562.2409. found: 562.2407; IR (KBr): 3054, 2929, 2337, 1342 cm$^{-1}$.

Example 33

Yield: 65%; yellow solid; m.p. 263-267° C.; $^1$H NMR (400 MHz, CDCl$_3$): δ 7.64 (d, J=1.6 Hz, 1H), 7.38-7.34 (m, 5H), 7.34-7.30 (m, 1H), 7.26-7.22 (m, 8H), 7.20-7.15 (m, 7H), 3.71 (s, 3H), 3.36 (s, 3H); $^{13}$C NMR (100 MHz, CDCl$_3$): δ 167.3, 166.8, 152.0, 150.7, 143.6, 141.3, 138.9, 138.0, 137.7, 137.0, 136.9, 135.2, 132.2, 130.6, 130.4, 130.1, 129.9, 128.7, 128.6, 128.5, 128.2, 128.1, 127.9, 127.8, 127.5, 126.9, 126.7, 126.6, 126.2, 122.9, 122.0, 118.8, 115.0, 52.1, 35.3; HRMS (EI$^+$) calculated for C$_{38}$H$_{28}$N$_2$O$_2$: 544.2151. found: 544.2158; IR (KBr): 3054, 2923, 2337, 1750, 1357 cm$^{-1}$.

Example 34

Yield: 72%; yellow solid; m.p. 274-277° C.; $^1$H NMR (400 MHz, CDCl$_3$): δ 7.52 (d, J=1.2 Hz, 1H), 7.41-7.29 (m, 6H), 7.24-7.13 (m, 12H), 7.05 (d, J=7.2 Hz, 2H), 6.99 (d, J=1.2 Hz, 1H), 3.38 (s, 3H), 2.32 (s, 3H); $^{13}$C NMR (100 MHz, CDCl$_3$): δ 199.0, 151.9, 150.7, 143.7, 141.2, 139.1, 138.0, 137.2, 136.5, 136.2, 135.2, 131.2, 131.1, 130.1, 129.9, 128.7, 128.5, 128.2, 128.1, 127.9, 127.3, 127.0, 126.8, 122.0, 118.9, 117.9, 113.6, 35.4, 29.6, 26.8; HRMS (EI$^+$) calculated for C$_{38}$H$_{28}$N$_2$O: 528.2202. Found: 528.2210; IR (KBr): 3054, 2932, 1680, 1343, 1203 cm$^{-1}$.

Example 35

Yield: 86%; yellow solid: m.p. 262-266° C.; $^1$H NMR (400 MHz, CDCl$_3$): δ 9.79 (s, 1H), 7.45 (d, J=1.2 Hz, 1H), 7.43-7.37 (m, 5H), 7.34-7.30 (m, 1H), 7.26-7.22 (m, 8H), 7.20-7.15 (m, 7H), 3.41 (s, 3H); $^{13}$C NMR (100 MHz, CDCl$_3$): δ 193.3, 152.2, 151.1, 144.0, 141.1, 139.4, 137.8, 137.7, 136.4, 135.1, 131.2, 131.1, 130.1, 129.8, 128.9, 128.6, 128.3, 128.2, 127.4, 127.1, 126.9, 122.6, 122.2, 121.1, 118.9, 113.2, 35.5; HRMS (EI$^+$) calculated for C$_{37}$H$_{26}$N$_2$O: 514.2045. found: 514.2049 IR (KBr): 3054, 2923, 1620, 1342, 950 cm$^{-1}$.

Example 36

Yield: 73%; yellow solid; m.p. 244-248° C.; $^1$H NMR (400 MHz, CDCl$_3$): δ 7.39-7.26 (m, 5H), 7.25-7.16 (m, 12H), 7.14-7.02 (m, 4H), 6.96 (d, J=8.0 Hz, 1H), 6.45 (bs, 1H), 3.89 (bs, 2H), 1.74 (q, J=7.6 Hz, 2H), 0.73 (t, J=7.6 Hz, 3H); $^{13}$C NMR (100 MHz, CDCl$_3$): δ 151.4, 149.6, 142.8, 141.7, 139.3, 138.8, 137.3, 136.6, 135.3, 131.4, 131.2, 131.1, 130.2, 130.1, 128.6, 128.3, 127.9, 127.8, 127.1, 126.6, 126.4, 121.1, 120.6, 118.6, 117.3, 115.0, 48.1, 29.6, 21.1, 11.2; HRMS (EI$^+$) calculated for C$_{38}$H$_{30}$N$_2$: 514.2409. found: 514.2412; IR (KBr): 3054, 2932, 2337, 1343 cm$^{-1}$.

Example 37

Yield: 15%; scarlet red solid; m.p. 265-268° C.; $^1$H NMR (500 MHz, CDCl$_3$): δ 7.52-7.50 (m, 5H), 7.47-7.38 (m, 2H), 7.28-7.19 (m, 10H), 7.12-7.06 (m, 5H), 7.05-6.96 (m, 5H), 6.92-6.88 (m, 2H), 6.80 (td, J=8.0, 2.0 Hz, 1H), 6.50-6.49 (m, 2H); $^{13}$C NMR (125 MHz, CDCl$_3$): δ 150.0, 149.3, 140.5, 138.6, 137.8, 137.6, 136.9, 136.8, 135.6, 135.2, 134.6, 131.8, 131.7, 131.2, 130.9, 130.2, 130.0, 129.7, 128.5, 128.2, 127.9, 126.9, 126.7, 126.6, 126.5, 125.9, 125.5, 124.9, 123.2, 121.8, 118.9, 117.5; HRMS (FAB$^+$) m/z: MH$^+$ calculated for C$_{49}$H$_{32}$N$_2$: 648.2565. Found: 648.2563; IR (KBr): 3054, 2929, 2337, 1342 cm$^{-1}$.

Determination of Absorption and Fluorescence Spectra:

An ultraviolet-visible absorption spectrum (solvent: dichloromethane; concentration: 10$^{-5}$ M) and a fluorescence spectrum (solvent: dichloromethane; concentration: 10$^{-4}$ M; excitation wavelength: 400 nm) for each of the 1,9-diazaphenalene derivatives obtained in Examples 9, 10, 12 and 18 were obtained using a Hitachi F-7000 fluorescence spectrophotometer. The results are shown in Table 4 and The FIG. 1.

TABLE 4

| Ex. | Absorption peak wavelength (nm) | Molar extinction coefficient (M$^{-1}$ cm$^{-1}$) | Fluorescence peak wavelength (nm) |
|---|---|---|---|
| 9 | 396, 434 | 18450, 18260 | 529 |
| 10 | 416 | 19700 | 519 |
| 12 | 392, 448 | 17290, 18720 | 517 |
| 18 | 430 | 13310 | 508 |

As shown in Table 4 and The FIG. 1, the fluorescence peak wavelengths of the 1,9-diazaphenalene derivatives obtained in Examples 9, 10, 12 and 18 range from 508 to 529 nm, and the FWHM (full width at half maximum) of the 1,9-diazaphenalene derivative obtained in Example 12 is about 75 nm, indicating that the 1,9-diazaphenalene derivative of the disclosure may emit green fluorescence after being excited.

In view of the aforesaid, the 1,9-diazaphenalene derivative of the disclosure, which contains a plurality of fused aryl rings and which is highly substituted, may emit fluorescence after being excited, and is thus suitable for use as a fluorescent material for an organic light emitting diode. Furthermore, the 1,9-diazaphenalene derivative of the disclosure may be manufactured in a high yield via a simple one-pot reaction.

While the disclosure has been described in connection with what is(are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A light-emitting composition, comprising
a 1,9-diazaphenalene derivative represented by formula (III),

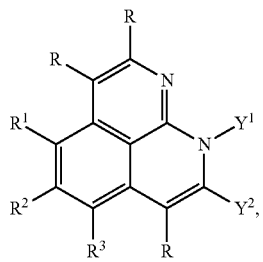

where
each R independently represents a $C_1$-$C_{10}$ linear or branched alkyl group, a phenyl group or a thiophenyl group, which is unsubstituted or substituted with a $C_1$-$C_{10}$ alkyl group, a $C_1$-$C_6$ alkoxy group, a $C_1$-$C_6$ haloalkyl group or a halo group;
each of $R^1$, $R^2$, and $R^3$ independently represents hydrogen, a $C_1$-$C_{10}$ linear or branched alkyl group, a $C_1$-$C_{10}$ alkoxy group, a $C_1$-$C_6$ haloalkyl group, an unsubstituted or $C_1$-$C_{10}$ alkyl group-substituted amino group, a halo group, a $C_6$-$C_{18}$ aryl group,

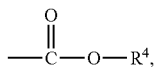

in which $R^4$ represents a $C_1$-$C_{10}$ alkyl group, or

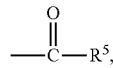

in which $R^5$ represents hydrogen or a $C_1$-$C_{10}$ alkyl group;
$Y^1$ represents hydrogen, or a $C_1$-$C_{10}$ linear or branched alkyl group; and
$Y^2$ represents R,
wherein said composition is light-emitting.

2. The light-emitting composition according to claim 1, wherein each R is independently selected from the group consisting of phenyl, 4-methylphenyl, 4-methoxyphenyl, 4-bromophenyl, 4-trifluoromethylphenyl and 2-thienyl.

3. A 1,9-diazaphenalene derivative represented by formula (III):

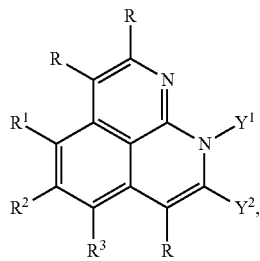

where
each R independently represents a $C_1$-$C_{10}$ linear or branched alkyl group, or a 5-6 membered aryl or heteroaryl group which is unsubstituted or substituted with a $C_1$-$C_{10}$ alkyl group, a $C_1$-$C_6$ alkoxy group, a $C_1$-$C_6$ haloalkyl group or a halo group;
each of $R^1$, $R^2$, and $R^3$ independently represents hydrogen, a $C_1$-$C_{10}$ linear or branched alkyl group, a $C_1$-$C_{10}$ alkoxy group, a $C_1$-$C_6$ haloalkyl group, an unsubstituted or $C_1$-$C_{10}$ alkyl group-substituted amino group, a halo group, a $C_6$-$C_{18}$ aryl group,

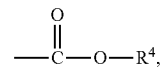

in which $R^4$ represents a $C_1$-$C_{10}$ alkyl group, or

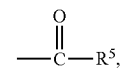

in which $R^5$ represents hydrogen or a $C_1$-$C_{10}$ alkyl group; and
$Y^1$ and $Y^2$ are combined to form a 6-membered ring moiety represented by

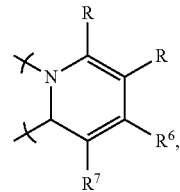

where
$R^6$ and $R^7$ are combined to form a 5-6 membered aryl or heteroaryl group represented by

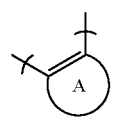

which is unsubstituted or substituted with a $C_1$-$C_{10}$ alkyl group, a $C_1$-$C_6$ alkoxy group, a $C_1$-$C_6$ haloalkyl group or a halo group.

4. The 1,9-diazaphenalene derivative according to claim 3, wherein $R^6$ and $R^7$ are combined to form a 5-6 membered aryl or heteroaryl group that is represented by

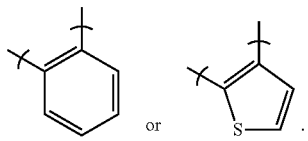 or .

5. The 1,9-diazaphenalene derivative according to claim 3, wherein each R is independently selected from the group consisting of phenyl, 4-methylphenyl, 4-methoxyphenyl, 4-bromophenyl, 4-trifluoromethylphenyl and 2-thienyl.

6. A process for manufacturing a 1,9-diazaphenalene derivative according to claim 3, comprising the step of subjecting a benzonitrile compound of formula (IV)

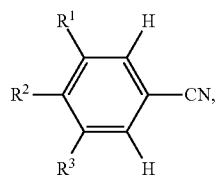
(IV)

an amine compound of formula X—NH$_2$ (V), where X represents hydrogen, hydroxyl or a C$_1$-C$_{10}$ linear or branched alkyl group, and an alkyne compound of formula (II)

$$\begin{array}{c} R \\ | \\ C \\ ||| \\ C \\ | \\ R \end{array} \qquad (II)$$

to a catalyst reaction in the presence of an oxidant and a catalyst selected from the group consisting of a rhodium salt and a ruthenium salt.

7. The process according to claim 6, wherein a molar ration of the benzonitrile compound to the alkyne compound ranges from 1:2 to 1:3.5.

* * * * *